United States Patent [19]
Stark

[11] Patent Number: 6,086,251
[45] Date of Patent: Jul. 11, 2000

[54] PROCESS FOR OPERATING A THERMOCOUPLE TO MEASURE VELOCITY OR THERMAL CONDUCTIVITY OF A GAS

[75] Inventor: Hartmut Stark, Stockelsdorf, Germany

[73] Assignee: Drager Medizintechnik GmbH, Germany

[21] Appl. No.: 09/074,774

[22] Filed: May 8, 1998

[30] Foreign Application Priority Data

Dec. 6, 1997 [DE] Germany .................. 197 54 198

[51] Int. Cl.[7] .................. G01N 25/18; G01N 7/02; G01P 5/10
[52] U.S. Cl. .................. 374/179; 374/44; 374/142; 374/148; 374/164; 73/204.24
[58] Field of Search .................. 374/44, 142, 179, 374/164, 148; 73/204.24

[56] References Cited

U.S. PATENT DOCUMENTS

| | | | |
|---|---|---|---|
| 1,766,149 | 6/1930 | Sawyer | 374/164 |
| 3,030,806 | 4/1962 | Davis | 73/204.24 |
| 3,071,520 | 1/1963 | Smalling | 73/204.24 |
| 3,485,099 | 12/1969 | Collins | 73/204.24 |
| 3,913,379 | 10/1975 | Rusz et al. | 73/23.21 |
| 5,043,560 | 8/1991 | Masreliez | 374/179 |
| 5,119,674 | 6/1992 | Nielsen | 73/204.24 |
| 5,677,484 | 10/1997 | Stark | 73/204.24 |

FOREIGN PATENT DOCUMENTS

| | | |
|---|---|---|
| 0 187 723 | 7/1986 | European Pat. Off. . |
| 469219 | 4/1975 | U.S.S.R. .................. 374/164 |
| 1530995 | 12/1975 | U.S.S.R. .................. 374/142 |
| 664094 | 5/1979 | U.S.S.R. .................. 374/44 |
| 2 297 164 | 7/1996 | United Kingdom . |
| WO 89/01132 | 2/1989 | WIPO . |

OTHER PUBLICATIONS

Hastings, C. E., "A new type instrument for measuring air velocity", AIEE Winter meeting paper 49–23, Dec. 1948.

*Primary Examiner*—Diego Gutierrez
*Assistant Examiner*—Stanley J. Pruchnic, Jr.
*Attorney, Agent, or Firm*—McGlew and Tuttle, PC

[57] ABSTRACT

A process for operating a thermocouple (2), which is arranged in a gas atmosphere and is maintained at a working temperature that is increased compared with the gas temperature by means of an a.c. power source (11). The determination of the thermal power introduced into the gas atmosphere and the temperature measurement are made possible with one measuring element. The thermocouple voltage is compared with a predetermined reference voltage $U_B$ arising from the working temperature of the thermocouple, a difference signal is formed between the thermocouple voltage and the reference voltage $U_B$, and the a.c. power source (11) is influenced with the difference signal such that the thermocouple voltage is maintained at a constant value relative to the reference voltage $U_B$.

15 Claims, 4 Drawing Sheets

PROCESS FOR OPERATING A THERMOCOUPLE TO MEASURE VELOCITY OR THERMAL CONDUCTIVITY OF A GAS

FIELD OF THE INVENTION

The present invention pertains to a process for operating a thermocouple, which is arranged in a gas atmosphere and is maintained at a working temperature that is increased compared with that of the gas atmosphere by means of an alternating current (a.c.) power source.

SUMMARY AND OBJECTS OF THE INVENTION

A device of this type has become known from EP 187 723. A thermocouple consisting of two parts made of different materials is connected to an a.c. power source to be heated to a predetermined working temperature. The variable to be measured is determined by evaluating the thermocouple voltage. To eliminate the a.c. voltage component superimposed to the thermocouple voltage, an evaluating element consisting of low-pass filters is connected to the terminals of the thermocouple. Certain physical features of the gas atmosphere surrounding the thermocouple shall be determined from the thermocouple voltage.

Furthermore, thermal measurement methods have been known, which are based on introducing a certain heating power into a gaseous medium while determining the temperature at the same time. Such a measurement process is used, e.g., in a hot wire anemometer. The measuring element proper is in direct thermal contact with the medium to be measured here, and the temperature difference between the medium being measured and the measuring element is controlled to a constant value. For the case of flow measurement, the heating power needed for temperature control is a direct measure of the flow velocity if the gas parameters are known. To make it possible to control the temperature difference between the medium being measured and the measuring element to the required constant value, the temperatures of the measuring element and of the medium being measured are usually determined separately and the excess temperature is calculated by difference formation in a downstream evaluating unit. While it is logical to utilize the temperature coefficient of the heat conductor to determine the temperature of the measuring element, it is possible to use, e.g., any temperature-dependent resistor to measure the temperature of the medium. However, the use of two elements of the same type, one of which is the active, intentionally heated element, while the second, passive element with a minimal evaluating current is used to measure the temperature of the medium, has become widespread in practice for reasons of symmetry.

However, this widely used arrangement has some drawbacks related to its principle. The temperature difference that is actually of interest, which directly affects the quality of the measurement, is generated by forming the difference between two comparatively large electric signals. Since the relative errors in the value of the difference increase in such a process, this difference signal responds very sensitively to disturbances in the individual measured values. This is compounded by the fact that the individual measured temperature values used to form the difference must first be determined by conversion from the measured resistance values. These resistance values are also affected by the contact resistances of the plug-type contacts present in the supply lines. Fluctuations in the contact resistances at the plug-type contacts affect the resistance of the heat conductor and of the temperature-measuring element in different ways, and the contact resistances may also change over time. If a resistance-measuring bridge is used to form the difference, frequent null balance is necessary because of the change in the resistances over time.

The fact that the temperature is obtained from the difference of two individual temperatures, one of which is substantially higher than the other, makes it necessary to separate the temperature-measuring points in space. If this requirement is not satisfied, thermal conduction through the medium and convection effects will considerably interfere with the independent measurement of the individual temperatures, especially in the range of low flow velocities. However, the separation of the temperature-measuring points in space would mean a larger size. In addition, it is not always guaranteed that the medium temperature measured reflects the conditions at the heated element in the case of a sufficient distance between the temperature-measuring points, because inhomogeneous temperature distributions in the flow cannot be ruled out. Such a hot-wire anemometer is described in U.S. Pat. No. 3,913,379.

SUMMARY AND OBJECTS OF THE INVENTION

The primary object of the present invention is to provide a measuring process which makes it possible to determine the thermal power introduced into a gas atmosphere while determining the temperature at the same time.

According to the invention, a process for operating a thermocouple is provided in which the thermocouple is arranged in a gas atmosphere, is maintained at a working temperature that is increased compared with the gas temperature by means of an a.c. (alternating current) power source, and is connected to an elimination element for separating the a.c. voltage from the thermocouple voltage. The thermocouple voltage is compared as the EMF (electromotive force) of the said thermocouple with a predetermined reference voltage $U_B$ arising from the working temperature. A difference signal is formed between the thermocouple voltage and the reference voltage $U_B$. The a.c. power source is influenced with the difference signal such that the thermocouple voltage is maintained at a constant value relative to the reference voltage $U_B$.

According to another aspect of the invention a process is provided for operating a thermocouple. The thermocouple is arranged in a gas atmosphere and is maintained at a working temperature that is increased compared with the gas atmosphere by means of an a.c. power source. The process includes measuring the thermocouple voltage as the EMF of the said thermocouple during the periods of time during which the a.c. power source is disconnected from the thermocouple by means of a switch The thermocouple voltage is compared with a predetermined reference voltage $U_B$ arising from the working temperature, and a difference signal is formed between the thermocouple voltage and the reference voltage $U_B$. The a.c. power source is influenced with the difference signal such that the thermocouple voltage is maintained at a constant value relative to the reference voltage $U_B$.

The advantage of the present invention is essentially that the thermocouple voltage generated at the thermocouple is used to control the temperature of the thermocouple in a thermocouple which is heated to a working temperature by means of an a.c. power source. A separate temperature-measuring device is no longer necessary due to the use of the thermocouple voltage for the temperature control.

The thermocouple voltage represents a voltage value whose magnitude is proportional to the temperature difference between the heated junction point in the middle of the wire and the two junction points at the supply wires. Since the junction points on the supply wires, which are also called the reference points, are essentially at the temperature level of the gas atmosphere, the separate temperature-measuring device can be abandoned.

Relative to the flow measurement with two measuring wires, the measurement process according to the present invention is characterized in that the error-prone determination of the temperature difference from two approximately equal measured quantities is eliminated. A signal proportional to the temperature difference is formed, instead, directly at the measurement site. Furthermore, the temperature difference signal as a thermocouple voltage is already available as an electric signal that can be subjected to further processing directly, which also makes the error-prone conversion of a resistance signal into temperature values unnecessary. The contact transition resistance and the specific resistance do not affect the transmission of the measured signal, because the signal is a pure voltage signal. Since only a feed line and a return line are necessary to supply the heating power and to take off the thermocouple voltage, the cabling becomes simplified, and the plug-type connections also become smaller at the same time. Besides advantages in terms of handling, this also leads to more favorable manufacturing costs.

The control of the temperature of a heating circuit according to the present invention can be used especially advantageously in a thermal infrared radiator, whose heating wire is composed of two parts made of different materials. The two parts are then wound such that the junction point of the parts is located approximately in the middle of the wire coil. The heat radiation properties can also be improved by the coils being coated with a ceramic coating.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
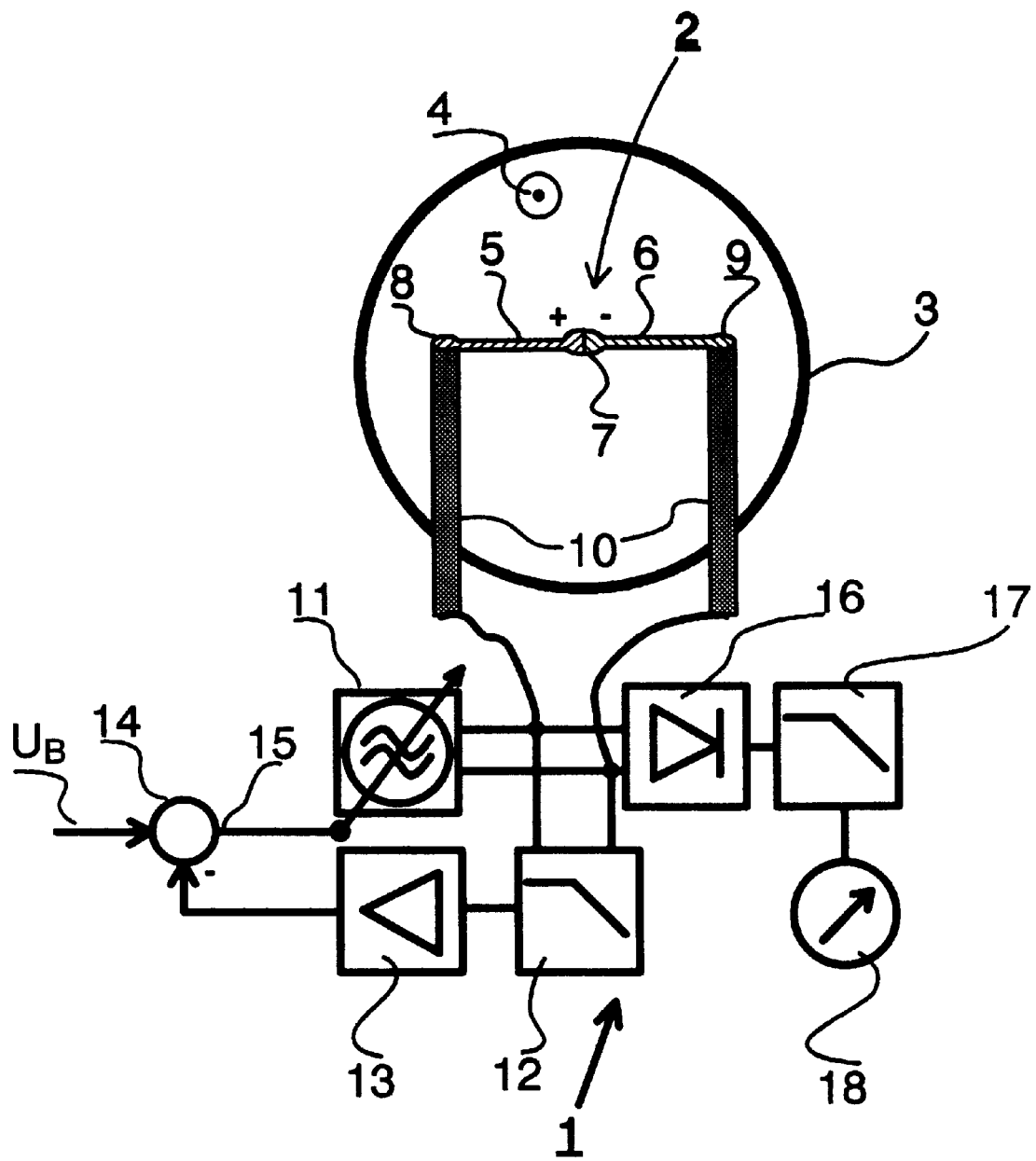
FIG. 1 is a schematic diagram showing a first measuring device arranged in a gas flow channel.

Referring to the drawings in particular, FIG. 1 schematically shows a first measuring device 1, in which a first thermocouple 2 is arranged in a gas flow channel 3. The flow through the gas flow channel 3 is along an axis 4 extending at right angles to the plane of the drawing. The first thermocouple 2 comprises a first part 5 made of Chromel, and a second part 6 made of Alumel, which abut against each other at a junction point 7 and are connected to supply wires 10 by means of additional junction points 8, 9. The first thermocouple 2 is connected to an a.c. power source 11 that is free from direct voltage and is heated by this to a working temperature that is increased compared with the temperature of the medium present in the gas flow channel. In this wiring of the first thermocouple 2, an a.c. voltage signal, to which a direct voltage caused by the intrinsic EMF of the first thermocouple 2, hereinafter called the thermocouple voltage, is superimposed, is present on the supply wires 10.

This thermocouple voltage is filtered out of the a.c. voltage signal by means of a low-pass filter 12 connected to the supply wires 10, which filter acts as an elimination element, is raised to a higher signal level with an amplifier 13, and is compared with a reference voltage $U_B$ at a subtraction element 14. As a temperature set point, the reference voltage $U_B$ is proportional to the working temperature of the first thermocouple 2. The difference signal present at the output 15 of the subtraction element 14, which is formed from the amplified thermocouple voltage and the reference voltage $U_B$, is sent as a correcting variable to the a.c. power source 11. The first thermocouple 2, the low-pass filter 12, the amplifier 13, the subtraction element 14, and the a.c. power source 11 together form a temperature control circuit of the first thermocouple 2, wherein the thermocouple voltage reflects the actual temperature value. In addition to the low-pass filter 12, a rectifier 16, which is followed by a smoothing means 17 and a display instrument 18, is connected to the supply wires 10. The display instrument 18 supplies a measured value that is proportional to the effective value of the amplitude of the a.c. voltage signal present on the supply wires 10.

The first measuring device 1 according to the present invention operates as follows:

In the case of a stagnant gas flow in the gas flow channel 3, a constant working temperature resulting from the reference voltage $U_B$ becomes established at the thermocouple 2, and a likewise constant deflection, which is set as the zero point for the stagnant gas flow, can be read on the display instrument 18. In the case of a gas flow differing from zero in the gas flow channel 3, the first thermocouple 2 initially cools, as a result of which the voltage of the a.c. power source 11 and consequently the heating power of the first thermocouple 2 are correspondingly increased until the original temperature has become reestablished. The deflection of the display instrument 18 also increases corresponding to the increase in the voltage, and the deflection related to the zero position is an indicator of the velocity of the flowing gas in the gas flow channel 3. The gas flow in the gas flow channel 3 can thus be determined in an especially simple manner. The first measuring device 1 is suitable for the determination of the thermal conductivity of the gas atmosphere surrounding the first thermocouple 2 in the case of a stagnant gas flow.

Figure 2:
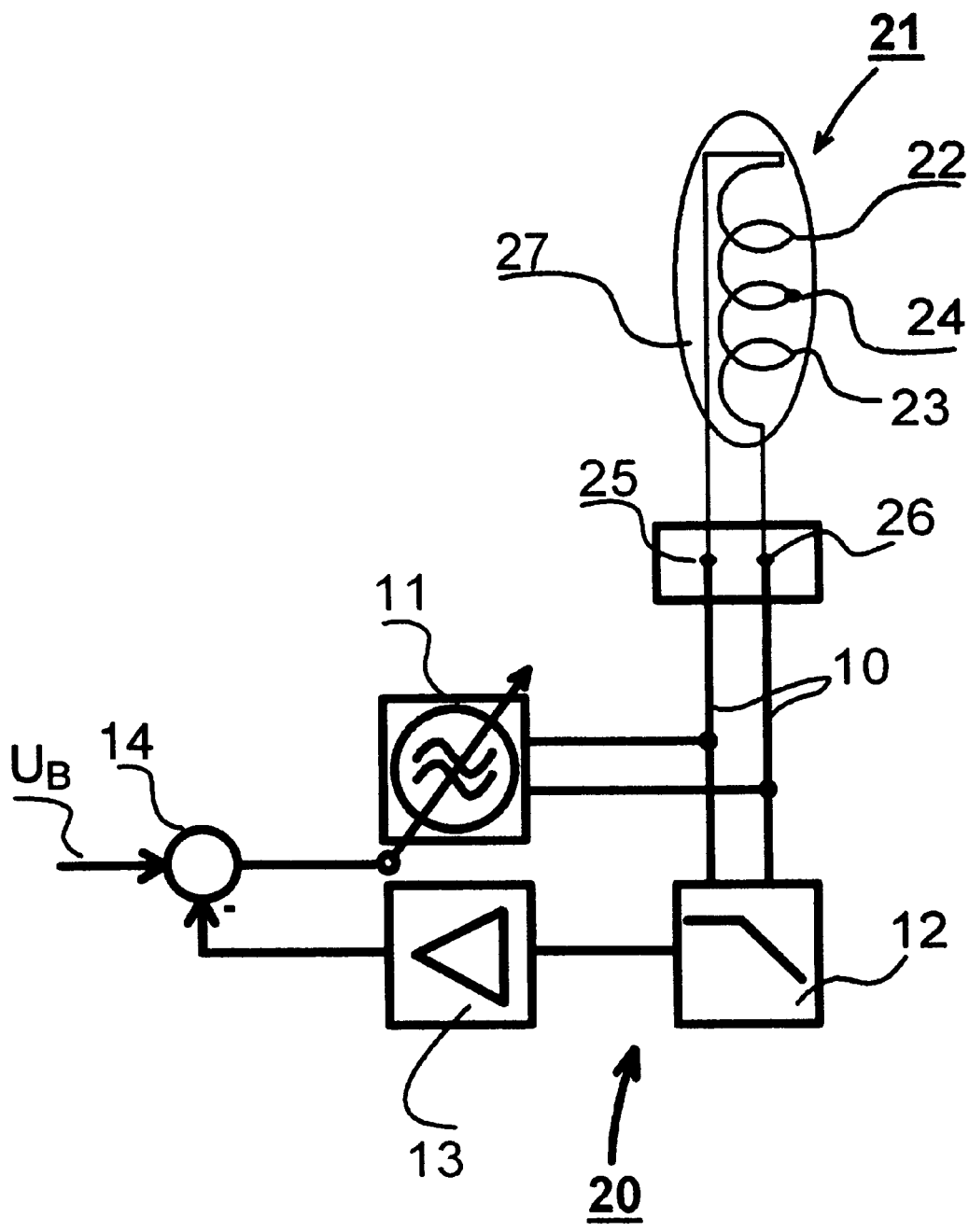
FIG. 2 is a schematic representation of a temperature-controlled infrared radiator.

FIG. 2 shows a schematic view of a temperature-controlled infrared radiator 20, with a second thermocouple 21, which is composed of two parts 22, 23 that consist of different materials. The parts 22, 23 are welded together at a junction point 24 and are connected at additional junction points 25, 26 to the supply wires 10. Identical components are designated with the same reference numbers as in FIG. 1. The parts 22, 23 of the second thermocouple 21 have a coil-shaped design. To increase the heat capacity of the infrared radiator 20, the parts 22, 23 and the junction point 24 are embedded in a ceramic mass 27.

The mode of operation of the infrared radiator 20 is based on the fact that the thermocouple voltage of the second thermocouple 21, which is proportional to the temperature of the second thermocouple 21, is separated from the heating a.c. voltage with the low-pass filter 12 and the amplifier 13 and is then subjected to further processing for the temperature control. The amplified thermocouple voltage is compared with the reference voltage $U_B$ at the subtraction element 14, the reference voltage $U_B$ being proportional to the temperature to be set.

Figure 3:
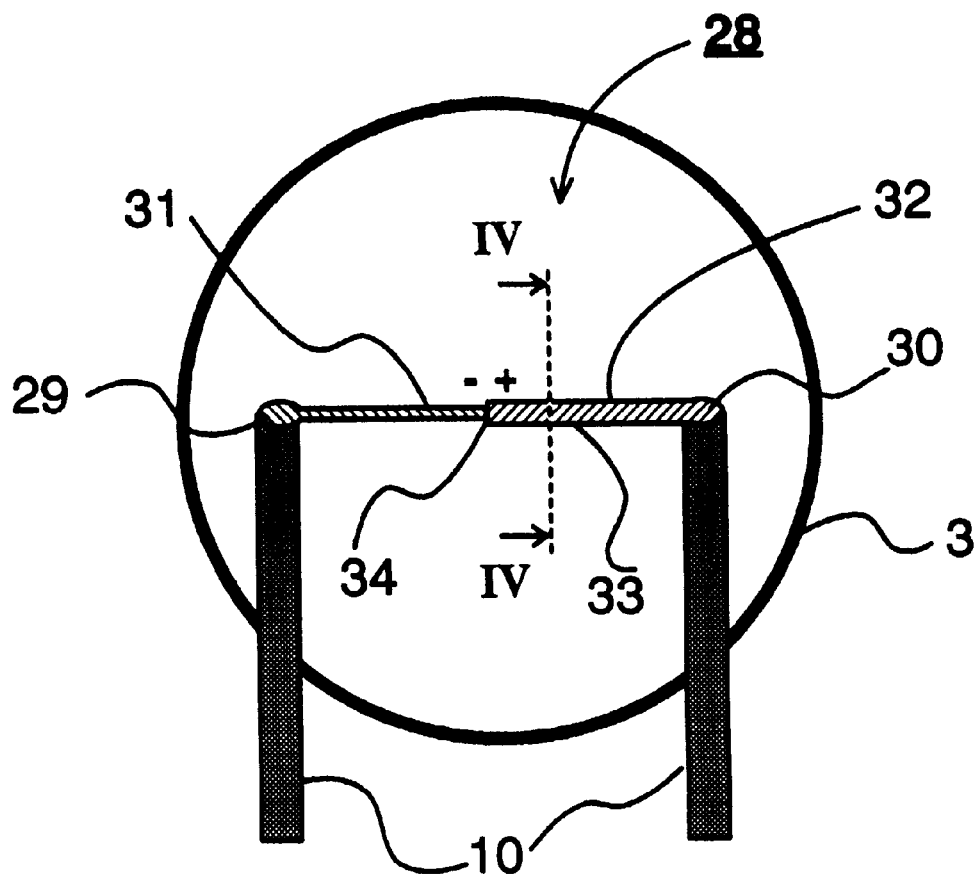
FIG. 3 is a schematic view showing a third thermocouple in a gas flow channel.

FIG. 3 schematically illustrates the design of a third thermocouple 28, in which a chromium-nickel wire 31 extending between two junction points 29, 30 is provided in a part 32 with a nickel coating 33. The nickel coating 33 extends approximately from the middle 34 of the wire 31 to the junction point 30. Identical components are designated with the same reference numbers as in FIG. 1. The nickel coating 33 may be prepared, e.g., by clamping the chromium-nickel wire 31 between the supply wires 10 and subsequently coating it half with pure nickel, e.g., by electroplating.

Figure 4:
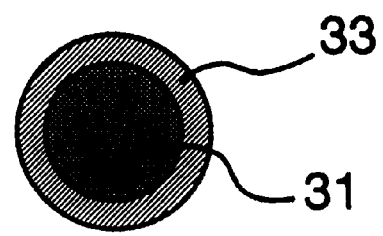
FIG. 4 is a sectional view showing the thermocouple according to FIG. 3 along section line IV—IV.

For greater clarity, FIG. 4 shows a sectional view of the chromium-nickel wire 31 with the nickel coating 33 along a section line IV—IV in FIG. 3.

Figure 5:
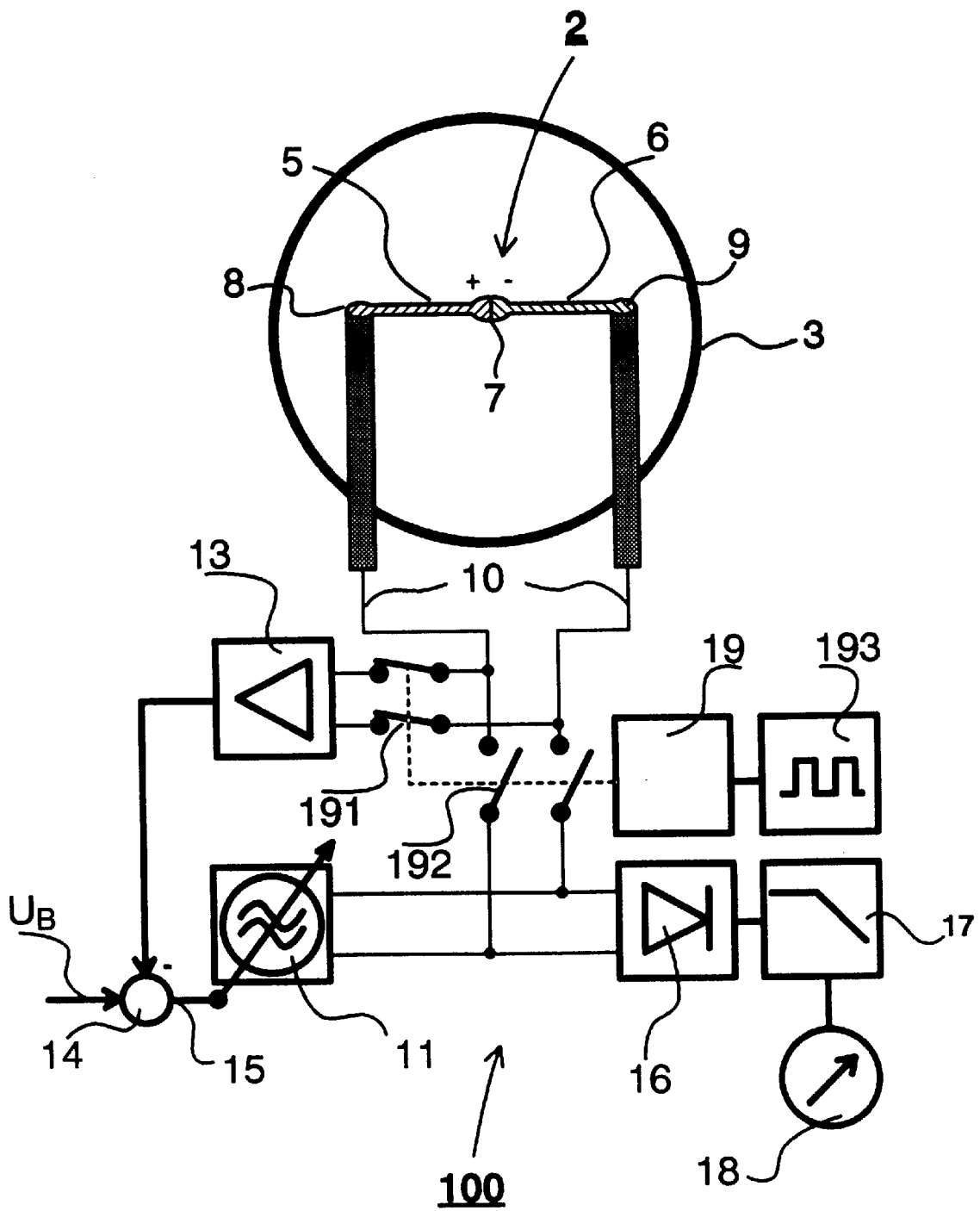
FIG. 5 is a schematic diagram showing a second measuring device arranged in a gas flow channel.

The second measuring device 100 shown in FIG. 5 is an alternative embodiment to the first measuring device 1 in FIG. 1. Identical components are designated with the same reference numbers as in FIG. 1. The heating current is cyclically interrupted by means of a switch 19, which has first switching contacts 191 in the line section between the amplifier 13 and the first thermocouple 2 and second switching contacts 192 in a line extending from the a.c. power source 11 to the first thermocouple 2. The thermocouple voltage is measured only during the time periods during which the a.c. power source 11 is disconnected from the first thermocouple 2. To cyclically interrupt the heating current, the switch 19 is activated by a square wave pulse generator 193 with changeover pulses. The point in time of the temperature measurement with the second measuring device 100 is illustrated in FIG. 5. The first switching contacts 191 are now closed and the second switching contacts 192 are opened. It is no longer necessary to filter out the thermocouple voltage from the a.c. voltage signal by means of the low-pass filter 12 in FIG. 1 due to the cyclic interruption of the heating current.

While a specific embodiment of the invention have been shown and described in detail to illustrate the application of the principles of the invention, it will be understood that the invention may be embodied otherwise without departing from such principles.

What is claimed is:

1. A process for operating a thermocouple, the process comprising the steps of:

arranging the thermocouple in a gas atmosphere;

maintaining the thermocouple at a working temperature that is increased compared with a temperature of the gas by means of a connection to an alternating current (a.c.) power source, the thermocouple having an a.c. component at the thermocouple, based on the connection to the power source with a superimposed thermocouple voltage originating from the EMF of the thermocouple;

connecting the thermocouple to an elimination element for separating the a.c. voltage from the thermocouple voltage;

comparing the thermocouple voltage, as the EMF of the thermocouple, with a predetermined reference voltage $U_B$ proportional to the working temperature of the thermocouple;

forming a difference signal between the thermocouple voltage and the reference voltage $U_B$; and influencing the voltage applied by the a.c. power source with the difference signal such that the thermocouple voltage is maintained at a constant value relative to the reference voltage $U_B$.

2. The process in accordance with claim 1, wherein a measured value that is proportional to a velocity of a gas flow of the gas atmosphere is determined from an amplitude of the a.c. component at the thermocouple arranged in a gas flow channel containing said gas atmosphere.

3. The process in accordance with claim 1, wherein a measured value that is proportional to the thermal conductivity of the gas atmosphere is determined from the amplitude of the a.c. voltage dropping over the thermocouple.

4. The process in accordance with claim 1, further comprising:

determining a first measured value that is proportional to the velocity of the gas flow from the amplitude of the a.c. component at the thermocouple arranged in a gas flow channel; and determining a second measured value that is proportional to the thermal conductivity of the gas atmosphere from the amplitude of the a.c. component at the thermocouple, said first and second measured values being formed by rectification of the a.c. component.

5. The process in accordance with claim 1, wherein said reference voltage $U_B$ is set at such a value that said thermocouple assumes a temperature suitable for the emission of an infrared radiation.

6. The process in accordance with claim 5, further comprising: using the thermocouple as an infrared radiator.

7. The process in accordance with claim 5, further comprising: providing the thermocouple with a ceramic coating such that two junction points are arranged outside the said ceramic coating.

8. The process for operating a thermocouple, the process comprising the steps of:

arranging the thermocouple in a gas atmosphere;

maintaining the thermocouple at a working temperature that is increased compared with the gas atmosphere by means of a connection to an alternating current (a.c.) power source to apply an a.c. voltage to the thermocouple;

disconnecting the thermocouple from the a.c. power source during periods of time by means of a switch;

measuring a thermocouple voltage over the thermocouple, as the EMF of the thermocouple, during the periods of time during which the a.c. power source is disconnected from the thermocouple;

comparing the thermocouple voltage with a predetermined reference voltage $U_B$ which is a function of the working temperature to form a difference signal between the thermocouple voltage and the reference voltage $U_B$; and influencing the voltage applied by the a.c. power source with the difference signal such that the thermocouple voltage is maintained at a constant value relative to the reference voltage $U_B$.

9. The process in accordance with claim 8, wherein a measured value that is proportional to velocity of gas flow is determined from an amplitude of the a.c. component at the thermocouple in the case of the thermocouple being arranged in a gas flow.

10. The process in accordance with claim 8, wherein a measured value that is proportional to the thermal conductivity of the gas atmosphere is determined from the amplitude of the a.c. component at the thermocouple.

11. The process in accordance with claim 8, further comprising the steps of:

determining a first measured value that is proportional to a velocity of gas flow of said gas atmosphere from the amplitude of the a.c. component at the thermocouple arranged in a gas flow channel;

determining a second measured value that is proportional to the thermal conductivity of the gas atmosphere from the amplitude of the a.c. voltage applied to the thermocouple; and forming said first measured value and said second measured value by rectification of the a.c. voltage.

12. A thermocouple device, comprising:

a first part made of a first material;

a second part made of a second material, said first part and said second part together forming a thermocouple wherein the thermocouple is arranged in a gas atmosphere;

an alternating current (a.c.) power source applying an a.c. voltage across the thermocouple for maintaining the thermocouple at a working temperature that is increased compared with a temperature of the gas;

an elimination element connected to the thermocouple for separating the a.c. voltage from a thermocouple voltage;

means for comparing the thermocouple voltage as the EMF of the thermocouple with a predetermined reference voltage $U_B$ proportional to the working temperature of the thermocouple;

means for forming a difference signal between the thermocouple voltage and the reference voltage $U_B$; and means for modulating the voltage applied by the a.c. power source with the difference signal such that the thermocouple voltage is maintained at a constant value relative to the reference voltage $U_B$.

13. The thermocouple device according to claim 12, further comprising:

a rectifier forming measured values by rectification of the a.c. voltage for determining a first measured value that is proportional to a velocity of gas flow from an amplitude of the a.c. component at the thermocouple arranged in a gas flow channel and determining a second measured value that is proportional to the thermal conductivity of the gas atmosphere from the amplitude of the a.c. voltage dropping over the thermocouple.

14. The thermocouple device according to claim 12, wherein said first part and said second part are connected to one another such that one of said first part and said second part are designed as a coating on a portion of the other of said first part and said second part.

15. The device in accordance with claim 12, wherein said reference voltage $U_B$ is set at such a value that said thermocouple assumes a temperature suitable for the emission of an infrared radiation and said thermocouple is provided with a ceramic coating such that two junction points are arranged outside said ceramic coating.

* * * * *

UNITED STATES PATENT AND TRADEMARK OFFICE
CERTIFICATE OF CORRECTION

PATENT NO. : 6,086,251
DATED : July 11, 2000
INVENTOR(S) : STARK

It is certified that error appears in the above-indentified patent and that said Letters Patent is hereby corrected as shown below:

Title page, item [73], should read--
Assignee: Dräger Medizintechnik GmbH --

Signed and Sealed this

Twenty-second Day of May, 2001

Attest:

NICHOLAS P. GODICI

*Attesting Officer*      *Acting Director of the United States Patent and Trademark Office*